United States Patent [19]

Ambike et al.

[11] Patent Number: 4,550,018

[45] Date of Patent: Oct. 29, 1985

[54] DENTAL HYGIENE COMPOSITIONS

[75] Inventors: Suhas H. Ambike, Westhill; Narinder S. Grewal, Scarborough; Eric Blaser, Toronto, all of Canada

[73] Assignee: Warner-Lambert Company, Morris Plains, N.J.

[21] Appl. No.: 655,275

[22] Filed: Sep. 26, 1984

Related U.S. Application Data

[62] Division of Ser. No. 350,671, Feb. 22, 1984, abandoned.

[51] Int. Cl.$^4$ .......................... A61K 7/16; A61K 7/18
[52] U.S. Cl. ...................................... 424/52; 424/49; 424/56
[58] Field of Search .................................... 424/49–58

[56] References Cited

U.S. PATENT DOCUMENTS

| | | | |
|---|---|---|---|
| 2,054,742 | 9/1936 | Elbel | 424/56 |
| 2,069,157 | 1/1937 | Sahyun | 424/57 |
| 2,236,828 | 4/1941 | Muncie | 424/56 |
| 2,689,170 | 9/1954 | King | 424/54 |
| 2,772,203 | 11/1956 | Salzmann | 424/54 |
| 2,772,204 | 11/1956 | King | 424/54 |
| 2,812,284 | 11/1957 | Sanders | 424/56 |
| 3,029,191 | 4/1962 | King | 424/52 |
| 3,256,155 | 6/1966 | Cahn et al. | 424/52 |
| 3,689,637 | 9/1972 | Pader | 424/52 |
| 3,692,894 | 9/1972 | Amo et al. | 424/56 |
| 3,840,657 | 10/1974 | Norpleet | 424/56 |
| 3,906,090 | 9/1975 | Colodney | 424/52 |
| 3,911,104 | 10/1975 | Harrison | 424/52 |
| 4,020,154 | 4/1977 | Perla et al. | 424/52 |
| 4,036,949 | 7/1977 | Colodney | 424/52 |
| 4,108,980 | 8/1978 | Duff | 424/57 |
| 4,150,151 | 4/1979 | Pader et al. | 424/56 |
| 4,235,874 | 11/1980 | Norpleet | 424/52 |
| 4,238,476 | 12/1980 | Harvey | 424/56 |
| 4,263,276 | 4/1981 | Harvey et al. | 424/52 |
| 4,264,580 | 4/1981 | Barberio | 424/56 |
| 4,301,141 | 11/1981 | Scheller | 424/49 |
| 4,314,990 | 2/1982 | Denny et al. | 424/52 |
| 4,340,583 | 7/1982 | Wason | 424/52 |
| 4,356,168 | 10/1982 | Harvey et al. | 424/52 |
| 4,357,313 | 11/1982 | Harvey et al. | 424/52 |
| 4,357,317 | 11/1982 | Weyn et al. | 424/52 |
| 4,363,794 | 12/1982 | Ochai et al. | 424/52 |

OTHER PUBLICATIONS

Sunstar C.A. 95#225487a (1981) of JPN, Kokai Tokkyo Koho 81 113709, Sep. 7, 1981.
Anon C.A. 85#25353k (1976) of Res. Discl. (1976) 144, 56.
Hassell et al., C.A. 75#18296j (1971) of Helv. Odontol. Acta (1971) 15(1): 52–3.
Van Betteray et al., C.A. 77#160630y (1972) of Caries Res. (1973) 7(1): 85–8.
Lim et al., C.A. 98#31322j (1983) of Caries Res. 1982, 16(6): 440–2.
Ishizeki et al., C.A. 78#67535g (1973) of Eisei Shikenjo Hokokuato (88) 75–8.
Sagihara et al. C.A. 91#198785e (1979) of Shika Kiso Ibakkai Zasshi 7719(3): 463–8.
Sugihara C.A. 92#28398j (1980) of J.S.C.C.J. (1979) 13(1): 18–24.
Ambike et al. C.A. 97#133371w (1982) of Canada 1,126,166 Jun. 22, 1982.

Primary Examiner—Shep K. Rose
Attorney, Agent, or Firm—Daniel A. Scola, Jr.; Gary M. Nath

[57] ABSTRACT

Dental hygiene compositions containing as antiplaque/antiseptic/deodorizing active ingredient highly pure alkali metal lauryl sulphate substantially free from non-lauryl alkyl salts.

6 Claims, No Drawings

DENTAL HYGIENE COMPOSITIONS

This is a divisional of application Ser. No. 350,671 Filed Feb. 22, 1984, now aband.

The present invention relates to dental hygiene compositions including, but not limited to, dentifrices in solid, powder, paste, or cream form and liquid mouth washes and rinses.

The primary use of such compositions is in maintaining dental hygiene and it is the function of such compositions to keep the surface of the teeth as clean and shiny as possible, to preserve the health of the teeth and gums, to inhibit the formation of unpleasant odours in the oral cavity and to freshen the user's breath. Known formulations of such compositions have been intended to provide cosmetic, cleansing, refreshing and/or deodorizing benefits, or have provided a therapeutic e.g. anticaries activity.

The compositions of the present invention are formulated to provide a further therapeutic activity, namely an antiplaque activity. Dental plaque is considered to be a material composed largely of microorganisms and an organic matrix derived from bacteria and saliva. Dental experts generally consider that the calculus also known as tartar is a mature plaque which has crystallized with the development of an identifiable crystal structure. It is well known that even with regular and thorough brushing, the plaque (i.e. calcified plaque) deposit adheres tenaciously to the teeth. Such deposits are unattractive and cause tooth decay.

It is the object of this invention to provide dental hygiene compositions, which will prevent or reduce the deposit of dental plaque. It is also an object of this invention to provide formulations containing anticaries agents such as sodium fluoride or sodium monofluorophosphate. A further object of this invention is to provide dental hygiene compositions which will possess significant antimicrobial properties.

The present invention is based on the finding that alkali metal salts of lauryl (dodecyl) sulphate when employed in a highly pure form, substantially free from other alkyl sulphates, exhibit particular advantages with respect to the formulation and use of dental hygiene compositions having antiplaque activity. The most readily-available lauryl sulphate salt is the sodium form, i.e. sodium lauryl sulphate. The potassium and other alkali metal salts are analogous to the sodium salt, although the use of the latter is normally preferred for reasons of economy. It will be appreciated, however, that the potassium and other alkali metal salts may be substituted for the sodium salt in the compositions of the invention and hereinafter described.

The material that is commonly commerically available under the designation "sodium lauryl sulphate" is not the pure compound sodium dodecyl sulphate $CH_3(CH_2)_{10}CH_2OSO_3Na$, but is a mixture of homologous sodium alkyl sulphates with sodium dodecyl sulphate predominating. Thus, as normally employed, the designation or chemical description "sodium lauryl sulphate" refers to a material containing as impurity varying amounts of sodium salts of non-dodecyl alkyl sulphates as well as the pure dodecyl sulphate salt. These materials often also contain varying amounts of sodium salts of inorganic acids e.g. sodium chloride and sodium sulphate, and unsulphated alcohols.

Sodium lauryl sulphate in impure form has been employed in the past in toothpaste compositions as a detergent or foam-producing agent. The present inventors have investigated the specific antimicrobial activity of solutions of various forms of material commercially available as "sodium lauryl sulphate", including one form that has recently become available from certain sources as a highly pure compound, substantially free from any content of non-dodecyl alkyl sulphate sodium salts. It has been found that the antimicrobial activity of the pure form of the sodium dodecyl sulphate material against the microorganisms considered to be responsible for plaque-formation in the human mouth is high, while the activity of the impure solutions combining substantial amounts of non-dodecyl alkyl sulphates against such microorganisms is inhibited to a significant extent.

Thus as between pure and impure solutions containing equivalent amounts of the pure compound, a higher specific activity will be exhibited by the solution that is substantially free of non-dodecyl alkyl sulphate salts, and therefore, by employing sodium dodecyl sulphate material in a form that is of high purity, there can be provided a composition having an effective level of antiplaque activity at a relatively lower content of the alkyl sulphate salt. The level of the alkyl sulphate is a matter of practical importance as the concentration of alkyl sulphate that needs to be employed in a mouthwash or toothpaste composition can be an important factor in the formation of a product that meets with consumer acceptance. In the mouth, sodium dodecyl sulphate and other alkyl sulphates have an astringent effect. Depending on the nature and proportions of the ingredients in the formulation, a small variation in the alkyl sulphate content can make the difference between a product that is acceptable to the consumer and one that is unacceptable as having a harsh and unpleasant taste or that gives an unpleasant sensation in the mouth owing to the physiological action of the alkyl sulphate on the mouth and dental tissues. Moreover, an excessive content of alkyl sulphate is normally to be avoided as in use of the composition this can lead to an over-abundant degree of foaming in the mouth.

The present invention provides a dental hygiene composition having antimicrobial activity against plaque-forming microorganisms and comprising an effective amount of from 0.1 to 2.0 per cent of one or more highly pure alkali metal salts of dodecyl sulphate substantially free from nondodecyl alkyl sulphate salts, dissolved in one or more vehicles physiologically compatible with the teeth and mouth tissues.

All parts and percentages herein are by weight unless specified otherwise.

Any suitably pure form of sodium dodecyl sulphate or other alkali metal dodecyl sulphate salt may be employed in the compositions of the invention. The amount of non-dodecyl impurity that can be tolerated in the composition without significantly detracting from the antiplaque activity depends in each case on the quantity of the pure sodium or the alkali metal dodecyl sulphate that is present, and the percentages of impurity are therefore best expressed in terms of the weight of alkali metal dodecyl sulphate. In the preferred forms, the compositions of the invention contain less than 5% of salts of non-dodecyl alkyl sulphate, based on the weight of alkali metal dodecyl sulphate, more preferably less than 2% and still more preferably less than 1% based on the weight of the alkali metal dodecyl sulphate salt. One especially preferred source of the alkali metal dodecyl sulphate salt for use in the composition of the invention is the highly pure form of sodium dodecyl sulphate that is available under the trade mark TEXA-PON L-100 from Henkel Chemicals (Canada) Ltd., Toronto, Canada. This material has a washing activity of 99%, indicating a content of pure sodium dodecyl sulphate of about 99%, and contains less than 0.6% of alkali metal chloride and sulphate and has a zero content of unsulphated alcohols. As far as the inventors are aware, the TEXAPON L-100 material is unique among other commercially-available forms of "sodium lauryl sulphate" in its high content of the pure dodecyl sulphate salt, but it will be appreciated that the invention is not necessarily limited to the use of the TEXAPON L-100 material and that such other highly pure forms of the dodecyl sulphate salt as may be available, or may be in the future become available, having a similar high degree of purity, preferably at least 95%, may be employed.

It may be noted that the preferred compositions are substantially free from any content of fatty acid - based soaps or detergents other than said dodecyl sulphate salts, as these may impart an undesirable taste without contributing to the antiplaque activity of the pure dodecyl sulphate salt, and therefore the desirable antiplaque activity of the compositions is exhibited to the best advantage when solutions free from these materials were employed.

The antimicrobial activity of the compositions of the invention varies with pH and the optimum activity of the dodecyl sulphate salts has been found to occur when the salts are acidulated to about pH 2. However, under extremely acid conditions, the alkali metal dodecyl sulphate salt tends to undergo hydrolysis so that the antiplaque activity diminishes over prolonged periods e.g. during storage. At pH in the range 3.0 to 5.0 satisfactory antiplaque activity can usually be achieved without undue loss of activity occurring during storage of the made-up compositions and therefore this range of pH is generally preferred. Optimum antiplaque activity extending over normal storage life can be obtained at about pH 4.5 and this pH is therefore most preferred for present purposes. However, in order to achieve this pH depending on the basicity of other ingredients of the composition, it may be necessary to add considerable quantities of aqueous solutions of acid, and in some formulations, particularly in the case of toothpastes and like solid or semi-solid dentifrices containing abrasives or other materials that exhibit a buffering action tending to maintain a pH higher than 4.5, the amount of liquid that can be added is limited owing to the requirement for a viscous consistency. In such cases pH somewhat higher than 4.5 will normally be employed, i.e. pH 4.5 to 5.0 consistent with maintaining a desired solids content in the composition. Any physiologically acceptable acid may be employed to adjust the pH to the desired value. Suitable examples include dilute hydrochloric acid and phosphoric acid. Physiologically acceptable acidic buffers e.g. buffering salt pairs such as the well-known acetate or citrate buffers i.e. sodium acetate-acetic acid buffer or sodium tricitrate/citric acid buffer, or buffer compounds such as dibasic sodium phosphate may be added, typically in an amount of about 0.01 to about 0.2%, to maintain the compositions at the desired pH during mixing and storage.

Certain types of liquid dental hygiene formulations, especially mouthwashes and rinses, conventionally contain substantial quantities of ethyl alcohol as an astringent and antiseptic agent. It has been found that in the presence of substantial quantities of alcohol the desired antiplaque activity can be achieved with a reduced content of the pure dodecyl sulphate salts of the invention, and it is suggested that the presence of ethyl alcohol potentiates the antiplaque activity of the dodecyl sulphate salts. Accordingly, in liquid mouthwash compositions containing substantial quantities of ethyl alcohol, in the range 10 to 30%, a somewhat smaller quantity of the alkali metal dodecyl sulphate salt may be employed, preferably in the range 0.1 to 0.5%.

The compositions of the invention may be flavoured with conventional essential oil flavours e.g. thymol, eucalyptol, methyl salicylate, and peppermint and spearmint oils, typically in an amount of 0.2 to 3.0%. In the case of compositions combining water or an aqueous vehicle, these oils may if necessary be maintained in dispersion with the aid of suitable dispersing agents. The use of cationic detergents is to be avoided for this purpose as these materials tend to reduce the efficacy of the alkali metal dodecyl sulphate salts and the preferred dispersing agents are nonionic surfactants advantageously in an amount to form 0.1 to 0.2%. As an example of a nonionic surfactant, there may be mentioned the water-soluble TWEEN (trade mark) materials, which are polyoxyethylene derivatives of fatty acid partial esters of sorbitol anhydrides, but these tend to have a pronounced taste that may not be desired in all instances and therefore the preferred nonionic surfactants are the water-soluble PLURONIC (trade mark) material available from BASF Wyandotte Corporation. These are alpha-hydro omega-hydroxy polyoxyethylene block copolymers. Especially preferred on account of its excellent dispersing and solubilizing activity and because it is relatively tasteless, is the PLURONIC F-127 nonionic surfactant which is available as a white solid, of average molecular weight 12,500, in prill or flake form.

In the case of compositions in accordance with the invention that are formulated as liquid mouthwashes or rinses, it is further preferred to add zinc chloride as an astringent, suitably in an amount of 0.01 to 0.05%. This material has mouth deodorizing activity and in presence of sodium dodecyl sulphate this activity is potentiated.

It has been further found that compositions containing a mixture of the pure alkali metal dodecyl sulphate together with alkali metal N-acyl sarcosinates exert a greater antiplaque activity than compositions containing equivalent weights of either of these compounds without the other, or that, in other words, the combination of the dodecyl sulphate salt with the N-acyl sarcosinate achieves a synergistic effect. For example, in comparisons of the antiplaque activity of five toothpaste compositions that contained 2% alkali metal dodecyl sulphate, 2% alkali metal N-acyl sarcosinate, and 2% of a mixture of the said sulphate and sarcosinate in the ratios 1:1, 1:2, and 2:1, respectively, there were observed percentage reductions of plaque of 50%, 40%, 78%, 61% and 60% respectively. This action of the N-acyl sarcosinates in potentiating the activity of the alkali metal dodecyl sulphates may be exploited in the formulation of toothpaste and like dentifrices in solid, powder, paste, or cream form, where a composition of high solids content with an enhanced antiplaque activity may be achieved at a relatively low content of the alkali metal dodecyl sulphate through inclusion of the N-acyl sarcosinate, in the formulation. The preferred material is sodium N-lauroyl sarcosinate added in an amount 0.5 to 2.0% by weight, more preferably in 1:1 to 1:3 ratio to the weight of alkali metal dodecyl sulphate, the latter preferably also being present in an amount of 0.5 to 2.0% by weight.

The composition may contain the conventional humectants such as glycerine and/or sorbitol. In the case of mouthwashes containing relatively large quantities of water e.g. in the range 50 to 90%, the humectants may be present in an amount up to about 20%, more typically about 10%. In the case of toothpaste and like products where the moisture content plays a more important role in preserving a desired consistency and viscosity of the product, somewhat greater quantities of humectant e.g. in the range 20 to 40% may be used.

Typically, toothpaste formulations in accordance with the invention will contain about 25 to 40% particulate dental abrasive, 1 to 4% thickener such as carboxymethyl cellulose derivatives and/or polyethylene glycols, together with the humectant, dodecyl sulphate salt, and N-acyl sarcosinate salt, if used, and may also contain a physiologically acceptable pigment, an artificial sweetener agent e.g. sodium saccharin or sodium cyclamate, an acid and buffer to maintain a desired pH, and an essential oil flavour.

Both the liquid and the solid or semi-solid, e.g. paste, formulations in accordance with the invention may contain small amounts of conventional fluoride anticaries agents. In the case of liquid mouthwashes or rinses this may suitably comprise sodium fluoride in an amount of 0.01 to 0.05% and in the case of toothpaste the preferred material is sodium monofluorophosphate in an amount of 0.5 to 2.0%, although other anticaries fluoride e.g. stannous fluoride or sodium fluoride may also be used.

Although the above description provides ample information for those skilled in the art to formulate dental hygiene formulation in accordance with the invention having antiplaque activity, for the avoidance of doubt certain specific formulations will be given, by way of example only, together with a test method for determining antiplaque activity.

EXAMPLE 1

The ingredients listed in Table 1 were mixed together in the percentages by weight indicated, to obtain a clear solution.

Table 1 also indicates preferred ranges of percentages by weight for the various ingredients.

EXAMPLE 2

The ingredients listed in Table 2 were blended together in the percentages by weight indicated, to yield a smooth paste.

Ranges of preferred percentages by weight are also indicated.

TABLE 1

| Ingredients | Percent | Preferred Range - Percent |
|---|---|---|
| Ethyl alcohol USP (95% v/v) | 20.0 | 10.0–30.0 |
| Zinc chloride USP | 0.02 | 0.01–0.05 |
| Glycerine USP (humectant) | 7.5 | 0.0–20.0 |
| Essential oil flavour | 0.2 | 0.2–3.0 |
| Texapon L-100* | 0.3 | 0.1–0.5 |
| Pluronic F-127 (trade mark) | 0.1 | 0.1–0.2 |
| Dye (colorant) | 0.003 | 0.002–0.005 |
| Hydrochloric Acid (10%) | 0.0003 | 0.0–0.0005 |
| Sodium citrate USP dihydrate | 0.028 | 0.025–0.04 |
| Citric acid USP anhydrous | 0.022 (Citrate Buffer) | 0.20–0.35 |
| Sodium Fluoride | 0.02 | 0.01–0.05 |
| Distilled water | Balance | 50–90 |
|  | 100.000 |  |

*(trade mark) - high purity sodium dodecyl sulphate available from Henkel Chemicals (Canada) Ltd.

TABLE 2

| Ingredients | Percent | Preferred Range - Percent |
|---|---|---|
| Precipitated silicon dioxide** | 32.0 | 25–40 |
| Sodium carboxymethyl cellulose (thickener) | 1.0 | 0.5–2.0 |
| Polyethylene glycol 4000 (thickener) | 1.0 | 0.5–2.0 |
| Titanium dioxide (pigment) | 1.0 | 0.5–3.0 |
| Texapon L-100* | 0.5 | 0.5–2.0 |
| Sodium N—lauryl sarcosinate | 1.0 | 0.5–2.0 |
| Glycerine (humectant) | 16.0 | 10.0–20 |
| Sorbitol (humectant) | 16.0 | 10.0–20 |
| Artificial sweetener (sodium saccharin or cyclamate) | 0.2 | 0.1–0.3 |
| Sodium monofluoro phosphate | 0.7 | 0.5–1.0 |
| Sodium phosphate dibasic (phosphate buffer) | 1.0 | 1.0–5.0 |
| Phosphoric acid | q.s. to adjust to pH 5 | q.s. to adjust to pH 3–6 |
| Essential oil flavour | 1.1 | 0.5–5 |
| Water | Balance | 20–40 |

*(trade mark) high purity sodium dodecyl sulphate available from Henkel Chemicals (Canada) Ltd.
**Precipitated silicon dioxide available from J.M. Huber Corporation, Harve de Grace, Maryland, U.S.A. under the trade mark ZEODENT 113, having a particle size from 100–300 angstrom units and a surface area from 10 m$^2$/g to 300 m$^2$/g

Test Method

The antimicrobial activity of sodium lauryl sulphate containing solutions can be determined as follows:

Tooth units are prepared in the form of 24×10×3 mm acrylic plastic tiles.

A medium is prepared comprising Trypticase soy broth obtained from Baltimore Biological Laboratories with 5% added sucrose sterilized by autoclaving in 500 ml quantities. The 500 ml quantities are then inoculated with a standard quantity of plaque-forming microorganisms. In successive tests, the inoculum consists of 0.5 ml from human saliva, and bacterial cultures of S. aureus St. faecalis, Ps. aeruginosa, E. coli, C. albicans, S. cerevisiae, and A. viscosus, each containing uniform number of cells, suitably of the order of 5×10$^8$ cells per inoculum. After inoculation, 10 ml aliquots are aseptically transferred to sterile 150×20 mm test tubes containing the plastic tiles. The tubes are incubated at 37° C. for 24 hours. The tubes are then shaken on a Vortex Mixer for 10 seconds to remove loose pellicle which is allowed to settle. The tiles are then transferred to test tubes containing the test solutions for 30 seconds and are then put into tubes containing sterile distilled water for the same period. Control tiles receive two 30 seconds treatment with sterile water. The tiles are then replaced into the test tubes containing inoculated medium broth and are incubated at 37° C. After 3 treatments, the plaque adhering on the tiles is measured employing a conventional chemical protein-determination procedure.

The embodiments of the invention in which an exclusive property or privilege is claimed are defined as follows:

1. A liquid mouthwash composition having antimicrobial activity against plaque forming microorganisms and comprising from 0.1 to 2.0 percent by weight of one or more highly pure alkali metal salts of dodecyl sulphate having less than 5% non-dodecyl alkyl sulphate salts, 0.5 to 2.0% by weight of alkali metal N-acyl sarcosinate, and a physiologically-acceptable acidic buffer at pH in the range of 3.0 to 5.0, dissolved in one or more vehicles physiologically compatible with the teeth and mouth tissues, and 10 to 30% by weight ethyl alcohol.

2. A liquid mouthwash composition as claimed in claim 1 containing 0.1 to 0.5% of said highly pure dodecyl sulphate salt.

3. A liquid mouthwash composition as claimed in claim 1 or 2 containing water or an aqueous vehicle, 0.2 to 3.0% by weight essential oil flavour and 0.1 to 0.2% by weight non-ionic surfactants as dispersing agent therefor.

4. A liquid mouthwash composition as claimed in claim 1 or 2 having a water content of 50 to 90% by weight and containing 0 to 20% by weight humectant.

5. A liquid mouthwash composition as claimed in claim 1 or 2 containing 0.01 to 0.05% by weight zinc chloride dissolved in water or an aqueous solution as said vehicle.

6. A liquid mouthwash composition as claimed in claim 1 comprising 0.1 to 0.5% of highly pure sodium dodecyl sulphate, 10 to 30% ethyl alcohol, 0.01 to 0.05% zinc chloride, 0 to 20% humectant, 0.2 to 3.0% essential oil flavour, 0.1 to 0.2 non-ionic dispersing agent, 0.002 to 0.005% dye, physiologically acceptable acid in an amount sufficient to bring the pH of the composition to pH 3.0 to 5.0, buffer solution for maintaining the pH of the composition at a pH in the range 3.0 to 5.0, 0.01 to 0.05% fluoride, anticaries agent and the balance water, all percentages being by weight.

* * * * *